US011490880B2

(12) United States Patent
Yap et al.

(10) Patent No.: US 11,490,880 B2
(45) Date of Patent: Nov. 8, 2022

(54) APPARATUS AND METHOD FOR BIOPSY AND THERAPY (71) Applicants: Biobot Surgical Pte. Ltd., Singapore (SG); Singapore Health Services Pte Ltd, Singapore (SG)

(72) Inventors: Chew Loong Yap, Singapore (SG); Yibao Shi, Singapore (SG); Teoh Hwa Ang, Singapore (SG); Poon Kiong Gilbert Mak, Singapore (SG); Hongjun Chen, Singapore (SG); Wai Sam Christopher Cheng, Singapore (SG); Shyi Peng Yuen, Singapore (SG); Sun Sien Henry Ho, Singapore (SG)

(*) Notice: Subject to any disclaimer, the term of this patent is extended or adjusted under 35 U.S.C. 154(b) by 433 days.

(21) Appl. No.: 16/685,688

(22) Filed: Nov. 15, 2019

(65) Prior Publication Data
US 2020/0077993 A1 Mar. 12, 2020

Related U.S. Application Data (62) Division of application No. 14/651,274, filed as application No. PCT/SG2013/000526 on Dec. 11, 2013, now abandoned.

(30) Foreign Application Priority Data

Dec. 11, 2012 (SG) .............................. 201209160-9

(51) Int. Cl.
*A61B 10/04* (2006.01)
*A61B 8/08* (2006.01)
(Continued)

(52) U.S. Cl.
CPC ............ *A61B 10/04* (2013.01); *A61B 8/0841* (2013.01); *A61B 8/12* (2013.01); *A61B 8/4209* (2013.01);
(Continued)

(58) Field of Classification Search
CPC ... A61B 10/04; A61B 10/0241; A61B 8/0841; A61B 8/12; A61B 8/4209;
(Continued)

(56) References Cited

U.S. PATENT DOCUMENTS 9,610,131 B2    4/2017   Stoianovici et al.
2002/0007103 A1  1/2002   Fontayne et al.
(Continued)

FOREIGN PATENT DOCUMENTS

WO    WO 2007/085953 A1    8/2007

OTHER PUBLICATIONS

International Search Report and Written Opinion for PCT/SG2013/000526, dated Jan. 30, 2014, 9 pgs.
(Continued)

*Primary Examiner* — Peter Luong
(74) *Attorney, Agent, or Firm* — Patterson Thuente Pedersen, P.A.

(57) ABSTRACT

A biopsy and therapy device comprising: a needling unit for holding and inserting a biopsy needle; an imaging module comprising an ultrasound probe and an actuator for moving the probe in a reciprocal action; a first arcuate slide; a second arcuate slide in sliding engagement with the first arcuate slide and a linkage to which the first arcuate slide is mounted; said linkage arranged to move the first and second arcuate slides within a vertical plane; said needling unit mounted to said arcuate slide wherein the first and second arcuate slides are mounted perpendicular to each other so as to rotate the needling unit about respective first and second principal axes.

9 Claims, 12 Drawing Sheets (51) Int. Cl.
   *A61B 8/12* (2006.01)
   *A61B 17/34* (2006.01)
   *A61B 8/00* (2006.01)
   *A61B 10/02* (2006.01)
   *A61B 17/00* (2006.01)

(52) U.S. Cl.
   CPC ...... *A61B 10/0241* (2013.01); *A61B 17/3403* (2013.01); *A61B 2010/0208* (2013.01); *A61B 2010/045* (2013.01); *A61B 2017/00274* (2013.01); *A61B 2017/3405* (2013.01); *A61B 2017/3409* (2013.01); *A61B 2017/3413* (2013.01)

(58) Field of Classification Search
   CPC ........ A61B 17/3403; A61B 2010/0208; A61B 10/045; A61B 2017/00274; A61B 2017/3405; A61B 2017/3409; A61B 2017/3413
   See application file for complete search history.

(56) References Cited

U.S. PATENT DOCUMENTS

| | | | |
|---|---|---|---|
| 2003/0018232 A1 | 1/2003 | Elliott et al. | |
| 2006/0229641 A1* | 10/2006 | Gupta | A61B 17/3403 606/130 |
| 2009/0030339 A1 | 1/2009 | Cheng et al. | |
| 2013/0282022 A1* | 10/2013 | Yousef | A61B 90/11 606/130 |
| 2015/0366544 A1 | 12/2015 | Yap et al. | |

OTHER PUBLICATIONS

Phee, L., et al., "Ultrasound guided robotic biopsy of the prostate", International Journal of Humanoid Robotics, vol. 3, No. 4, 2006, pp. 463-483.

Phee, L., et al., "Ultrasound Guided Robotic System for Transperineal Biopsy of the Prostate", Proceedings of the 2005 IEEE International Conference on Robotics and Automation, Barcelona, Spain, Apr. 2005, pp. 1315-1320.

Application and File History for U.S. Appl. No. 14/651,274, filed Jun. 11, 2015, applicants Yap et al.

* cited by examiner

APPARATUS AND METHOD FOR BIOPSY AND THERAPY

RELATED APPLICATIONS

The present application is a Divisional of U.S. patent application Ser. No. 14/651,274, filed Jun. 11, 2015, which is a National Phase entry of, and claims priority to, PCT Application No. PCT/SG2013/000526, filed Dec. 11, 2013, which claims priority to Singapore Patent Application No. 201209160-9, filed Dec. 11, 2012, all of which are incorporated by reference herein.

FIELD OF THE INVENTION

The present invention relates to the biopsy and therapy of a patient. In particular, the invention relates to methods and apparatus for the automatic conduct of such biopsy and therapy.

BACKGROUND

A prostate needle biopsy is recommended when prostate cancer is suspected. It is a surgical procedure in which a small sample of tissue is removed from the prostate gland and examined under the microscope by a pathologist, a doctor specializing in identifying disease through the study of cells, tissues and organs. The procedure takes about 15 minutes and is usually performed by an urologist with the use of a transrectal ultrasound (TRUS) probe. With the help of TRUS, a doctor guides a biopsy gun- a hand-held device with a spring-loaded, slender needle-through the wall of the rectum into the area of the prostate gland that appears abnormal.

The rectal wall is thin, so it is possible to place the needle accurately into the abnormal site of the prostate gland with the use of a biopsy gun with less injury to other tissues. When the biopsy gun is activated, the needle can remove a slender cylinder of tissue (about 1 mm by 18 mm), called a core, in a fraction of a second. Biopsy needles are tiny—only 1.2 mm in diameter, and about 200 mm long. A sliding sheath on the gun opens once the needle enters the prostate, closes onto a sample of tissue and the needle is withdrawn.

However, the current practice for prostate biopsies may include:
1. Random biopsy sites: The maximum total volume of tissue samples retrieved can be calculated to be, for example, about 220 mm3 in a 14-core method and the volume size of a typical prostate with a diameter of 40 mm is about 33,500 $mm^3$. Therefore, the biopsy cores represent only about 0.6% of the prostate in terms of volume. Without having accurate knowledge of the cancer site(s), it is unlikely that a random biopsy protocol will yield consistently high cancer detection rates.
2. Inaccurate needling: Although the biopsy is guided by TRUS, it is known that the biopsy needle may not reach the desired position accurately and quickly under manual control. Depending on the skills and experience of the urologist, inaccuracies in terms of centimeters are common occurrences.
3. Movement of prostate: During the biopsy, the translational motion or any motion of TRUS in the rectum will result in the movement of the prostate. As such the exact location in the prostate where cells are being extracted for diagnosis can no longer be precisely determined.
4. Limited 2D guidance: The TRUS used for biopsy guidance is 2D ultrasound images. As the biopsy sites are distributed in 3D, it is difficult for the surgeon to imagine the overall picture of the biopsy sites and to identify the biopsy site accurately and intuitively.
5. Transrectal: As most of the cancer occurs at the apex area of the prostate, a transperineal biopsy is considered to have a higher chance of obtaining cancer tissue, compared with the conventional transrectal biopsy. Furthermore, a transperineal biopsy is considered "cleaner", as its puncture point is on the skin, rather than on the rectum.
6. Multiple entry points for the needle: Using the transrectal approach, the number of holes that will be pierced through the walls of the rectum will be determined by the number of biopsy samples. Multiple insertion points through the walls of the rectum will also increase the chance of infection due to the presence of harmful substances in the rectum. Upon detection of cancerous cells in the tissue, therapy is then conducted on the patient.

During therapy, many skin punctures may result during the delivery of radioactive seeds into the prostate. Thus, there is a need to develop an invention that addresses the above mentioned short-comings of the current prostate biopsy and therapy environment.

SUMMARY OF INVENTION

In a first aspect, the invention provides a biopsy and therapy device comprising: a needling unit for holding and inserting a biopsy needle; an imaging module comprising an ultrasound probe and an actuator for moving the probe in a reciprocal action; a first arcuate slide; a second arcuate slide in sliding engagement with the first arcuate slide and a linkage to which the first arcuate slide is mounted; said linkage arranged to move the first and second arcuate slides within a vertical plane; said needling unit mounted to said arcuate slide wherein the first and second arcuate slides are mounted perpendicular to each other so as to rotate the needling unit about respective first and second principal axes.

In a second aspect the invention provides a biopsy and therapy device comprising: a 10 needling unit for holding and inserting a biopsy needle; an imaging module comprising an ultrasound probe and an actuator for moving the probe in a reciprocal action; an arcuate slide mounted to a first linear slide; a rotational linkage in sliding engagement with the arcuate slide; said first linear slide arranged to move the arcuate slide parallel to a first principal axis; said first linear slide mounted to a second linear side, said second linear slide arranged to move the first linear side parallel to a second principal axis; said needling unit mounted to said rotational linkage wherein the arcuate slide and rotational linkage are mounted perpendicular to each other so as to rotate the needling unit about said first and second principal axes.

In a third aspect, the invention provides a biopsy and therapy device comprising: a needling unit for holding and inserting a biopsy needle; an imaging module comprising an ultrasound probe and an actuator for moving the probe in a reciprocal action; an arcuate slide and a parallel linkage to which the arcuate slide is mounted; a rotational linkage in sliding engagement with the arcuate slide; said parallel linkage arranged to move the arcuate slide and rotational linkage within a vertical plane; said needling unit mounted to said arcuate slide wherein the arcuate slide and rotational linkage are mounted perpendicular to each other so as to rotate the needling unit about respective first and second principal axes.

The design of the biopsy and therapy apparatus according to the present invention enables the biopsy needling unit to move in both Cartesian and Polar coordinates. This concept eliminates the need for multiple punctures on the skin when many samples of the tissues are required to be extracted from the organ for diagnosis. In addition lesser entry points for the needle mean that risk of infection for the patient will be greatly minimized.

The combination of Polar and Cartesian capabilities of this invention, allows multiple conical motion envelopes to be developed depending on the needs of the operation. The ability of the apparatus to develop multiple conical envelopes is highly advantageous for operations especially in the prostate biopsy environment because insertion of the needle into the organ may be hindered by pubic bone.

In one embodiment, the pivot point for the conical envelope is located at the contact point of the needling unit, such that prior to insertion of the needle, the pivot point is effectively on the surface of the skin of the patient, In conventional methodology or previous invention, the pivot point is usually located inside the needling unit itself. When the pivot point is located inside the needling unit, slight movements in one end of the unit will result in movements in the other end of the unit which can be a major cause for concern during an operation as this will affect the accuracy of the system. Thus the concept of virtual pivot point ensures that accuracy of the system will not be affected by any unwanted or residual movements on the needling unit. The accuracy of the system is further increased as the distance between the pivot point and the organ to be diagnosed is now shorter, thus minimizing the error of the needle deviating from its intended trajectory.

In one embodiment, the device may include a needle sheath. Said needle sheath may comprise a thin stainless steel rod with enlarged protrusion at both ends said needle sheath may be loaded into the needling unit thereby creating a tunnel to guide the orientation and trajectory of the biopsy gun to the organ. A needle sheath may eliminate the risk of contamination to the needling unit during the extraction of blood tissues from the organ by the biopsy gun. To further reduce the possibility of such contamination from taking place, the needling unit may include a blot or recess to allow side loading of a single piece needle sheath instead of loading a two-piece needle sheath-through the front and back of the needling unit. Thus side loading may reduce cross contamination and decrease the set up time of the system.

In a further embodiment, the device may include a motorized needle stopper to determine the pre-calculated needle depth based on the imaging data from ultrasound probe or other means of imaging devices enhances the accuracy and reliability of the biopsy. Conventional biopsies are conducted manually leading to a lack of accuracy. Moreover using a motorized needle stopper enables a specific point in the organ to be identified for the extraction of blood samples for diagnosis.

To prevent contamination of the apparatus by the patient during the operation, a clear drape may be mounted over the apparatus during operation and engaged with a groove like retainer mechanism integrated onto the needling unit. This creates a barrier between apparatus and patient so that there is no cross contamination.

During a biopsy or therapy, the prostate may be immobilized despite the translational motion of the TRUS using an ultrasound probe sheath. This allows a pre-determined point in the prostate, where the needle will be able target for the extraction of tissue and resulting in a more reliable biopsy outcome.

In one embodiment, the first and second arcuate slides may be concentric about a pivot point. In this way, any movement of the needling unit by one or both arcuate slides does not affect the location of the contact point of the needling unit.

In a further embodiment, the pivot point may be located at a contact point of the needling unit.

In one embodiment, the needling unit may include a needle holder for holding a needle during insertion, said holder including a recess for receiving a needle in a direction transverse to the direction of insertion.

In one embodiment, said needling unit may include a needle stopper arranged to set a pre-determined depth of penetration of said needle, and so having a means to automatically prevent over insertion, or alternatively automatically insert the needle to a location determined through a prior examination.

In one embodiment, the device may include a drape for covering said biopsy and therapy device, said needling unit including a recess with which the drape is arranged to engage. In this way, the device is protected from cross contamination. Having an engagement recess also ensures a seal for better protection.

In one embodiment, the imaging module may include a probe sheath positioned on said 10 probe and arranged to allow relative reciprocal motion with said probe. Having the probe sheath on the probe allows the sheath to be inserted into the patient and acting as a brace against variation caused by the movement of the probe.

In one embodiment, said device may be arranged to conduct a biopsy and therapy procedure based upon one or more of the parameters: a needle insertion point defined as a coordinate position within said vertical plane, a first angle relative to the first principal axis, a second angle relative to the second principal axis and a depth of penetration of the needle. The device may therefore have the flexibility to operate under one or more specific parameters. Using all parameters, the device may position the contact point to a specific insertion point of the patient. Based on a prior examination the specific angle from each principal axis may also provide the best approach to the desired location, such as a tumour. The depth of penetration may then direct the needle to precisely the location required. The device according to this embodiment may therefore have all the relevant parameters pre-programmed, allowing the imaging unit to merely track the expected progress of the needle.

In a further embodiment, the invention provides a biopsy and therapy device comprising: a needling unit for holding and inserting a biopsy needle; an imaging module comprising an ultrasound probe and an actuator for moving the probe in a reciprocal action; an arcuate slide mounted to a first linear slide; a rotational linkage in sliding engagement with the arcuate slide; said first linear slide arranged to move the arcuate slide parallel to a first principal axis; said first linear slide mounted to a second linear side, said second linear slide arranged to move the first linear side parallel to a second principal axis; said needling unit mounted to said rotational linkage wherein the arcuate slide and rotational linkage are mounted perpendicular to each other so as to rotate the needling unit about said first and second principal axes.

BRIEF DESCRIPTION OF THE DRAWINGS

It will be convenient to further describe the present invention with respect to the accompanying drawings that illustrate possible arrangements of the, invention. Other arrangements of the invention are possible and consequently, the particularity of the accompanying drawings is not to be understood as superseding the generality of the preceding description of the invention.

DETAILED DESCRIPTION

Figure 1:
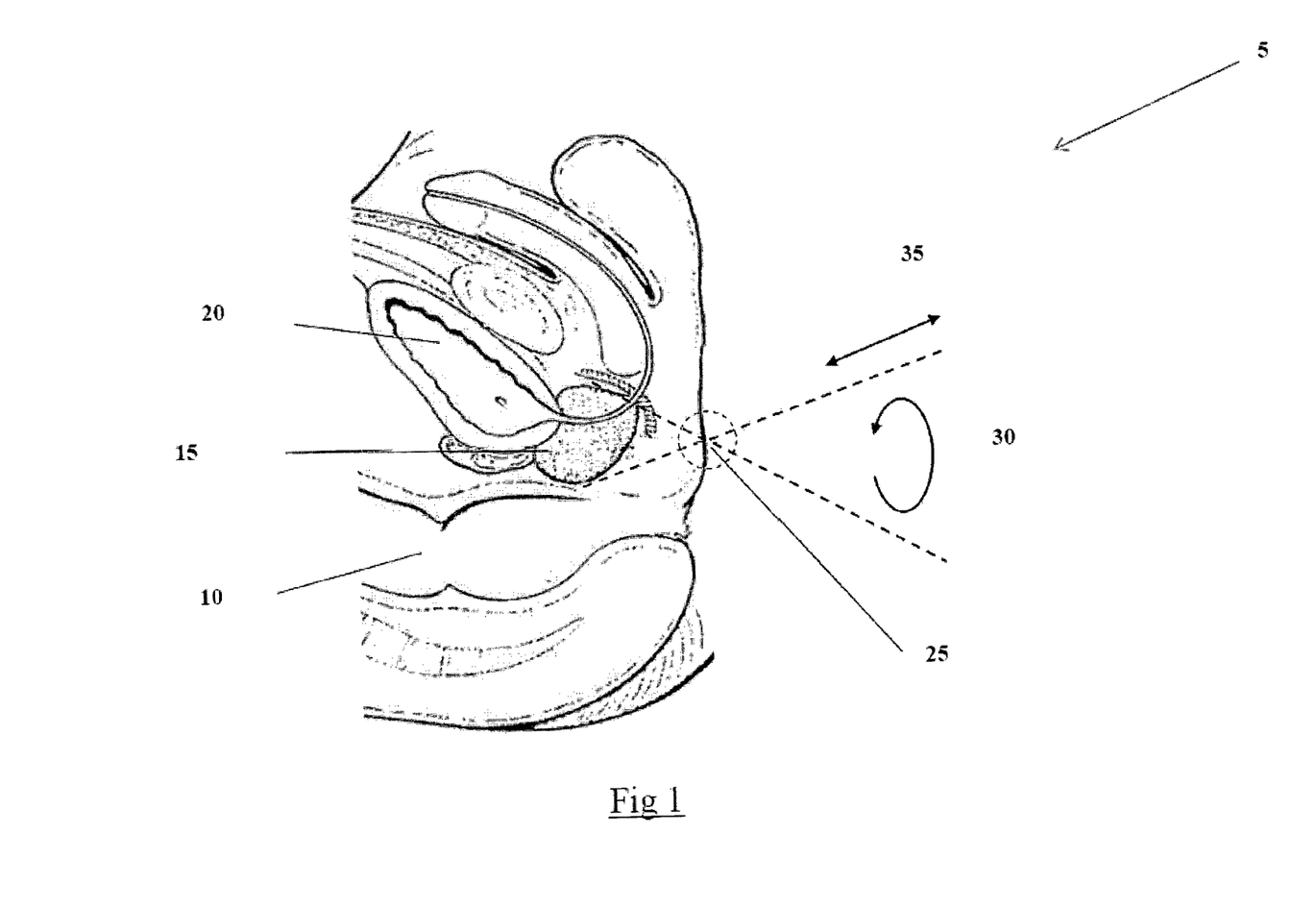
FIG. 1 is a cross sectional view of a patient indicating a point of entry for a needle to the prostate.
Figure 2:
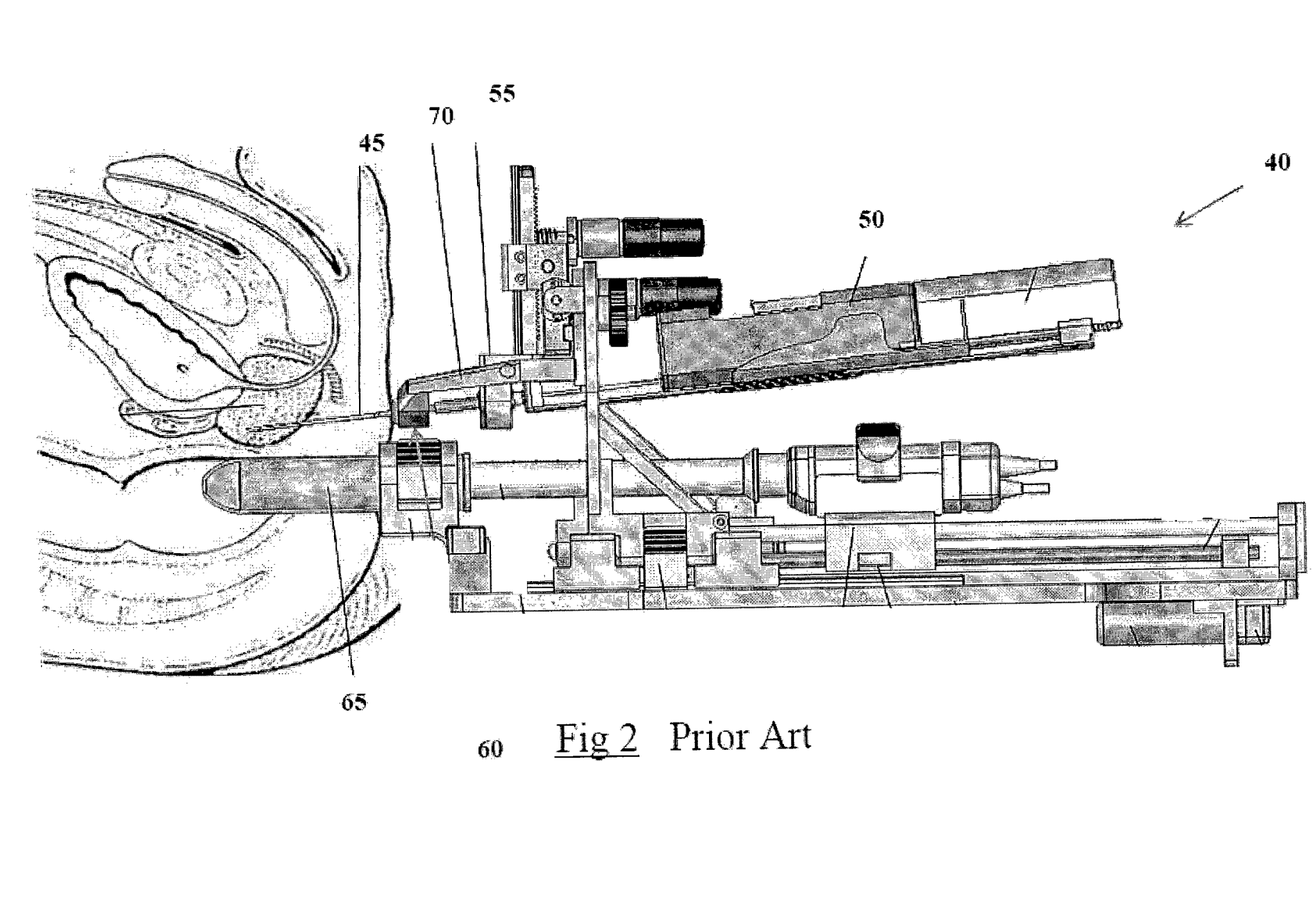
FIG. 2 is an elevation view of a biopsy and therapy device according to the prior art.

FIG. 1 shows a cross sectional view of a patient 5 indicating the rectum 10 prostate 15 and bladder 20. Further, for the purposes of a biopsy, FIG. 1 shows a pivot point 25 adjacent to the perineal in order to create a conical envelope 30 so as to position a device to take the biopsy through the insertion 35 of a needle at the pivot point 25. A device 40 of the prior art shown in FIG. 2 whereby a needle 45 is inserted at a pivot point guided by an ultrasound probe 65 inserted into the rectum 10. The needle 45 is inserted into the prostate 15 in order to extract material. The conical envelope of FIG. 1 is provided by two pivot points 55, 60. The needling unit 50 is moved subject to motions attached to the device 40 which move the needling device along linear slides which due to the pivots 55, 60 have the potential to rotate the needling device and consequently the needle 45 around a conical envelope. The point of rotation of the needle, that is the pivot point, becomes the front ball joint 60 which is proximate to but not at the surface of the perineal wall. It follows that by placing the needling unit 50 against the perineal wall, then rotating the needling unit so as to position the needle 45 for insertion, the offset between the ball joint 60 and the perineal wall represents a potential error in the placement of the needle. The probe 65 will identify this offset requiring a further iteration in order to place the needling unit 50 in a correct position as a result of the offset between the joint 60 and the perineal wall. This adds to the set up time not to mention the anxiety of the patient and the potential for error should the operator not wish to undertake sufficient iterations in order to get a perfect placement of the needle 45.

Figure 3:
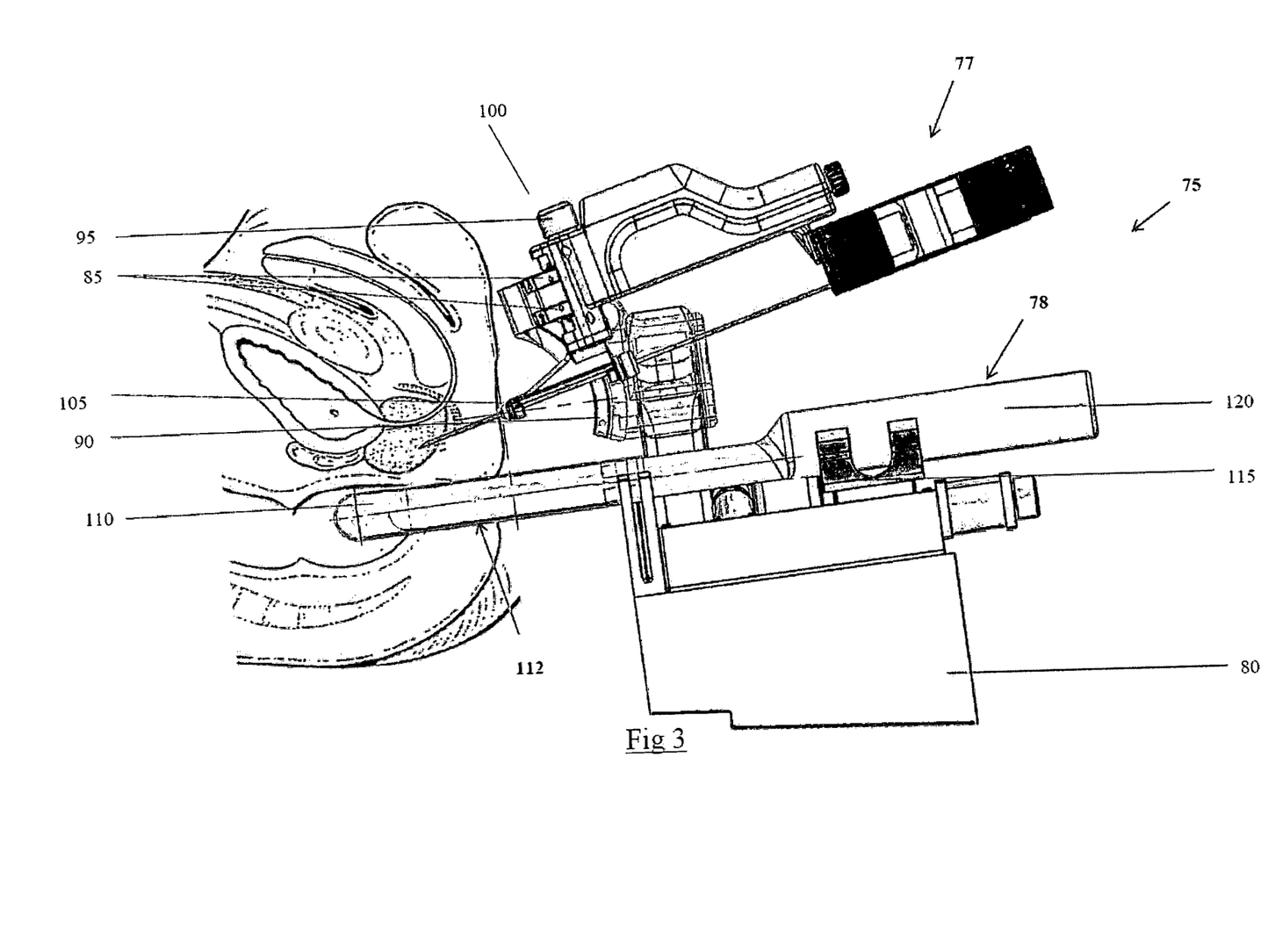
FIG. 3 is an elevation view of a biopsy and therapy device according to one embodiment of the present invention.

FIG. 3 is a side view of a biopsy and therapy device 75 according to one embodiment of the present invention. The figure shows the needle entry, with the apparatus comprising:

i. a needling unit 77 that is capable of both Conical and Cartesian approach of reaching the prostate through the perineal wall and ii. an imaging unit 78 that comprises of the ultrasound probe 112, probe holder 115 as well as ultrasound probe sheath 110.

Figure 4:
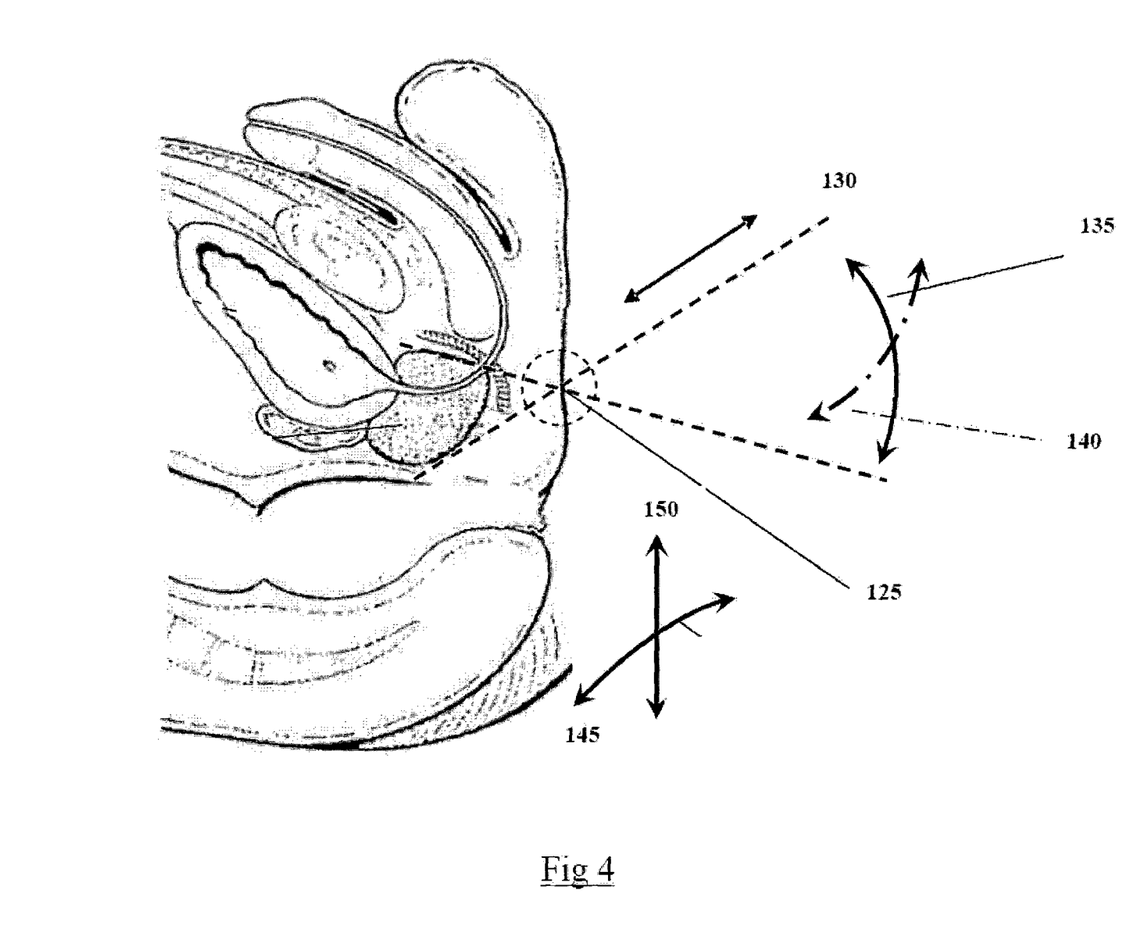
FIG. 4 is a cross sectional view of a patient indicating the pivot point for entry to the patient.

FIG. 4 is a drawing from a sectional view showing:

i. a Conical approach of reaching the prostate through the perineal wall, using the Y-axis rotation 140 that is, rotation about the Y-axis, and X-axis rotation 135 that is, rotation about the X-axis, of the needling unit and ii. a Cartesian approach of reaching the prostate through the perineal wall as the needling unit is able to maneuver in the up and down direction 150 and left and right direction 145.

Figure 5:
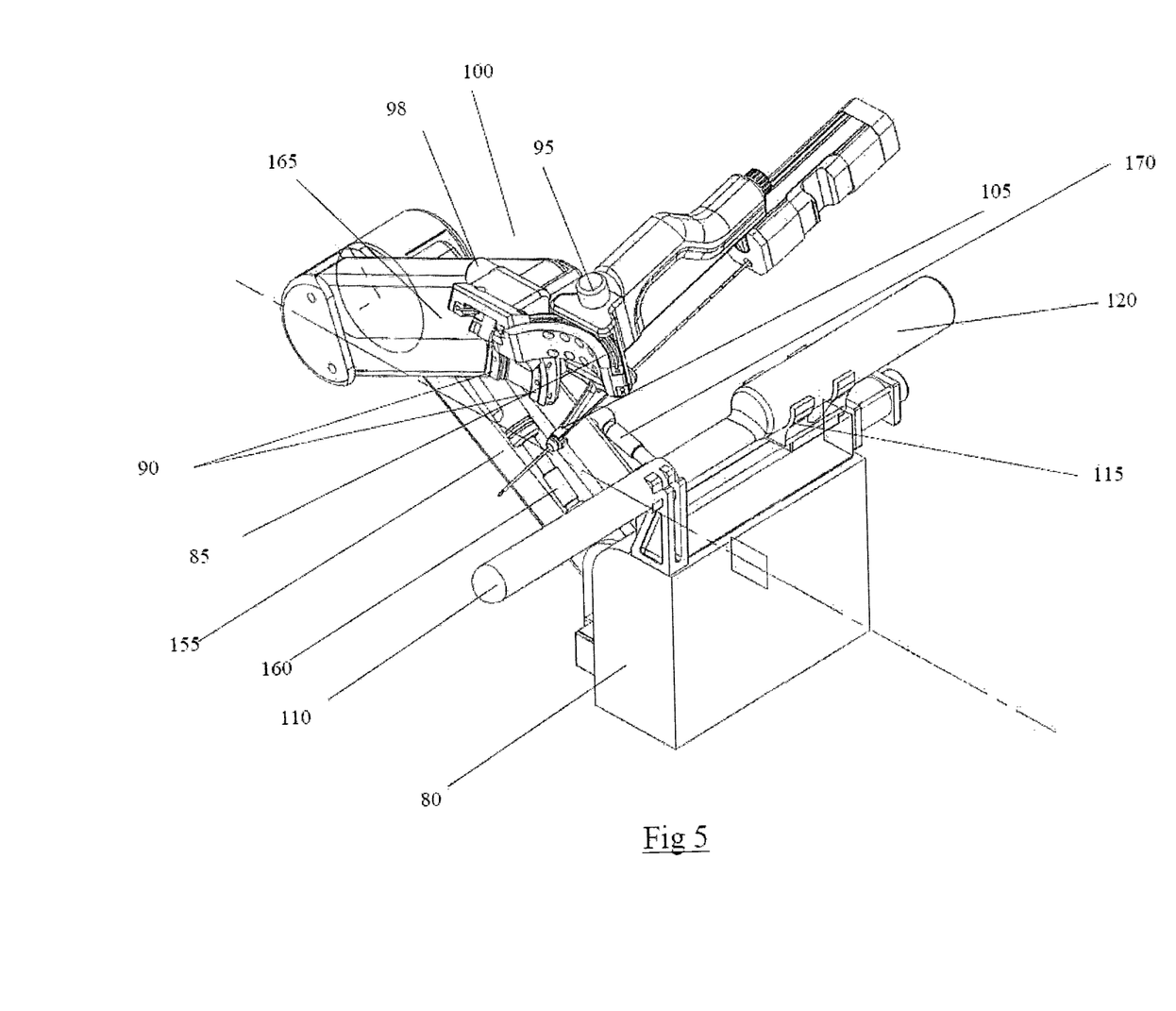
FIG. 5 is an isometric view of a biopsy and therapy device according to a further embodiment of the present invention.
Figure 6:
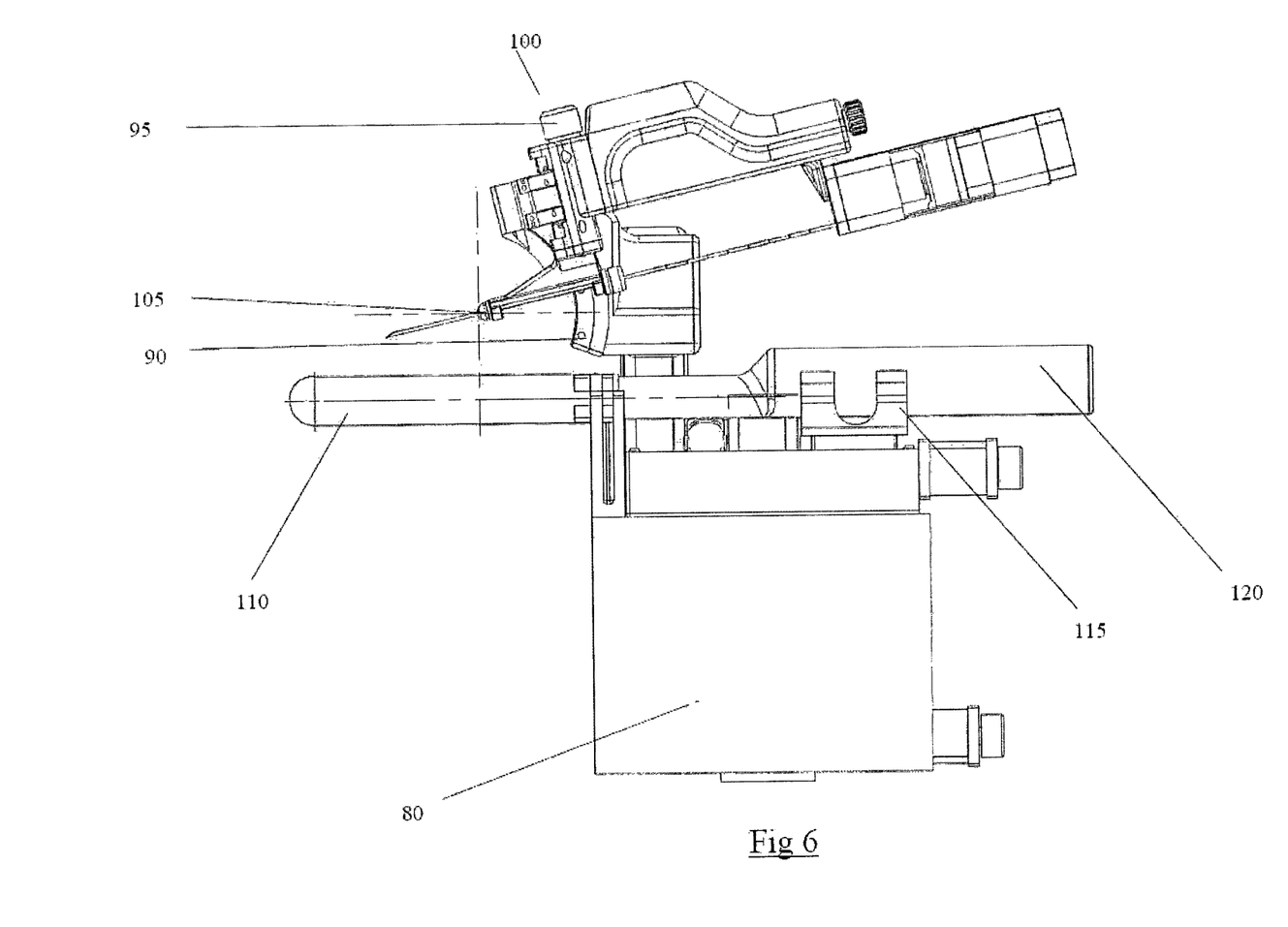
FIG. 6 is an elevation view of the biopsy and therapy device of FIG. 5.
Figure 7:
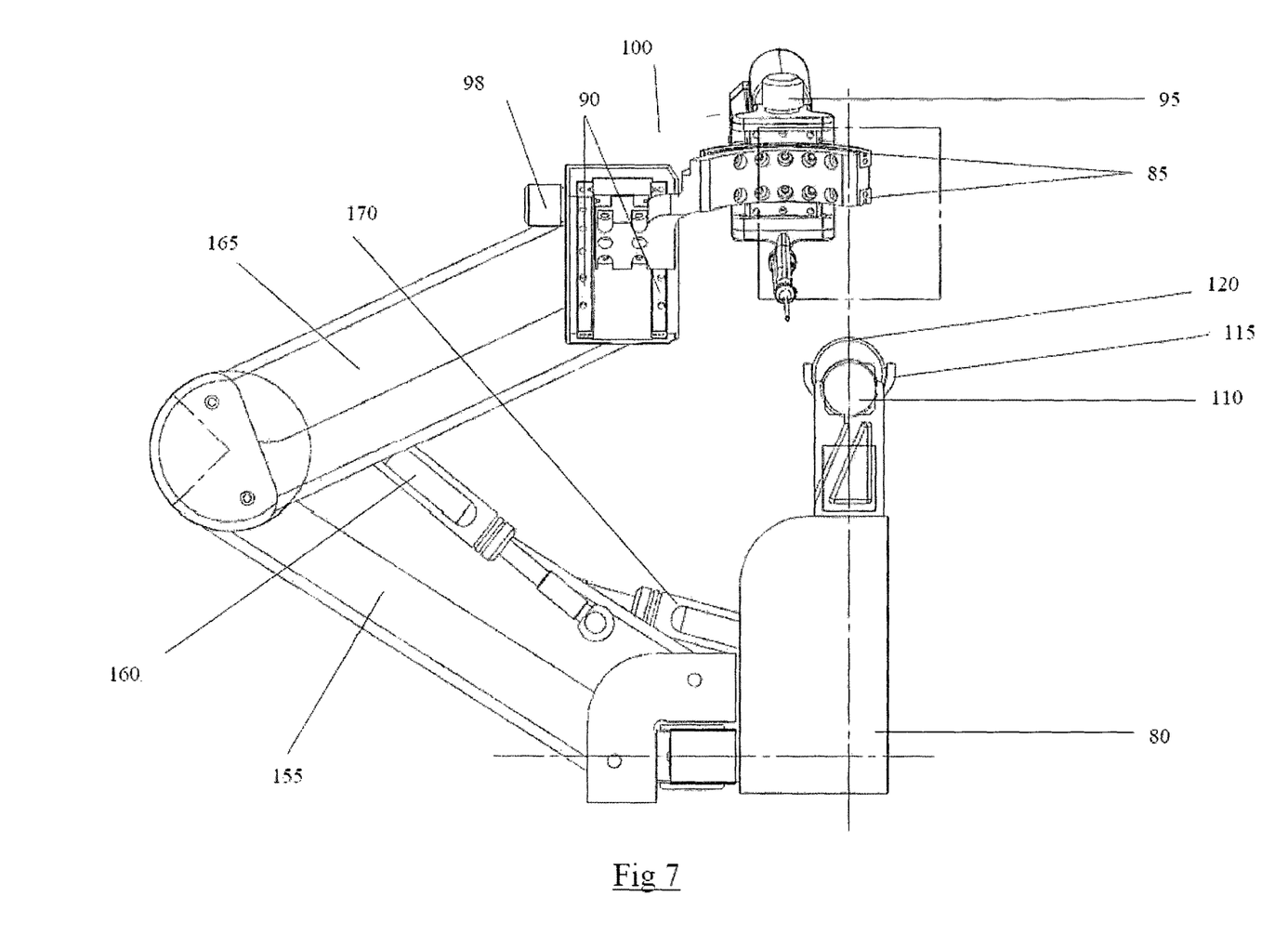
FIG. 7 is a front elevation view of the biopsy and therapy device of FIG. 5.

FIGS. 5, 6 and 7 show the apparatus using line schematics. In FIG. 5, the apparatus is mounted on a supporting platform 80 which may be moved so as to be proximate to the patient. The Y-axis rotation 140 of the needling unit is achieved by a pair of upper and lower radial sliding bearings or first arcuate slide (85), where this pair of radial sliding bearing is driven by a micro drive (95). The X-axis rotation 135 of the needling unit is achieved by a pair of upper and lower radial sliding bearing, or second arcuate slide (90), where this pair of radial sliding bearing is driven by a micro drive (98). These four sub units will form an assembly called the rotary head (100). The design and concept of this rotary head enables the whole needling unit to rotate about a common virtual pivot point thereby enhancing the reliability of the equipment during biopsy.

A needle sheath holding mechanism (105) is built into the needling unit so that the needle sheath is side-loaded, that is, loaded in a direction transverse to the direction of insertion of the needle. This makes the transfer and replacement of needles easier and more accessible and so minimizes the risk of cross contamination of blood samples from different patients.

FIG. 6 is side view of the apparatus using line schematics. The imaging unit comprises of an ultrasound probe sheath (110), where it is used to immobilize the prostate when the ultrasound image of the prostate is acquired by an ultrasound probe (120). The ultrasound probe is mounted on a probe holder (115).

FIG. 7 is a frontal view of the apparatus using line schematics. The up and down vertical movement of the needling unit is controlled by a parallel linkage (155) and a motorized linear actuator (160). The left and right horizontal movement of the needling unit is controlled by a parallel link (165) and a motorized linear actuator (117). The parallel links (155) and (165) ensures that the rotary head (100) stays in an upright position even if the needling unit moves in curved trajectory on the Y-axis plane.

Figure 8:
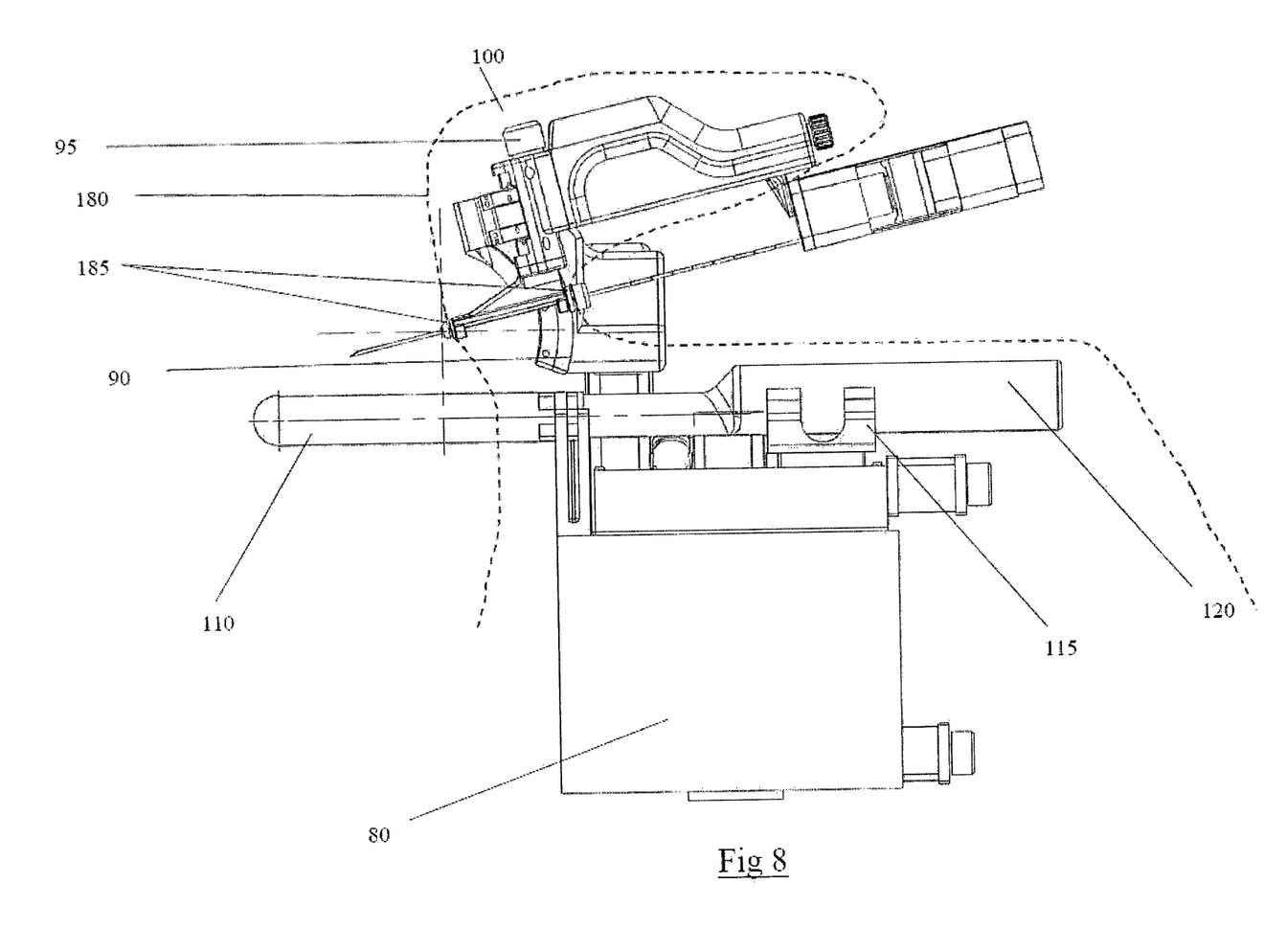
FIG. 8 is an elevation view of a biopsy and therapy device according to a further embodiment of the present invention.

FIG. 8 is side view of the apparatus using line schematics, which a clear plastic drape (180) is used to cover the biopsy device. The clear plastic drape (160) is securely engaged with the device using a recess, which in this case is a pair of groove retaining mechanism (185), to prevent any cross contamination between the apparatus and the patient.

Figure 9:
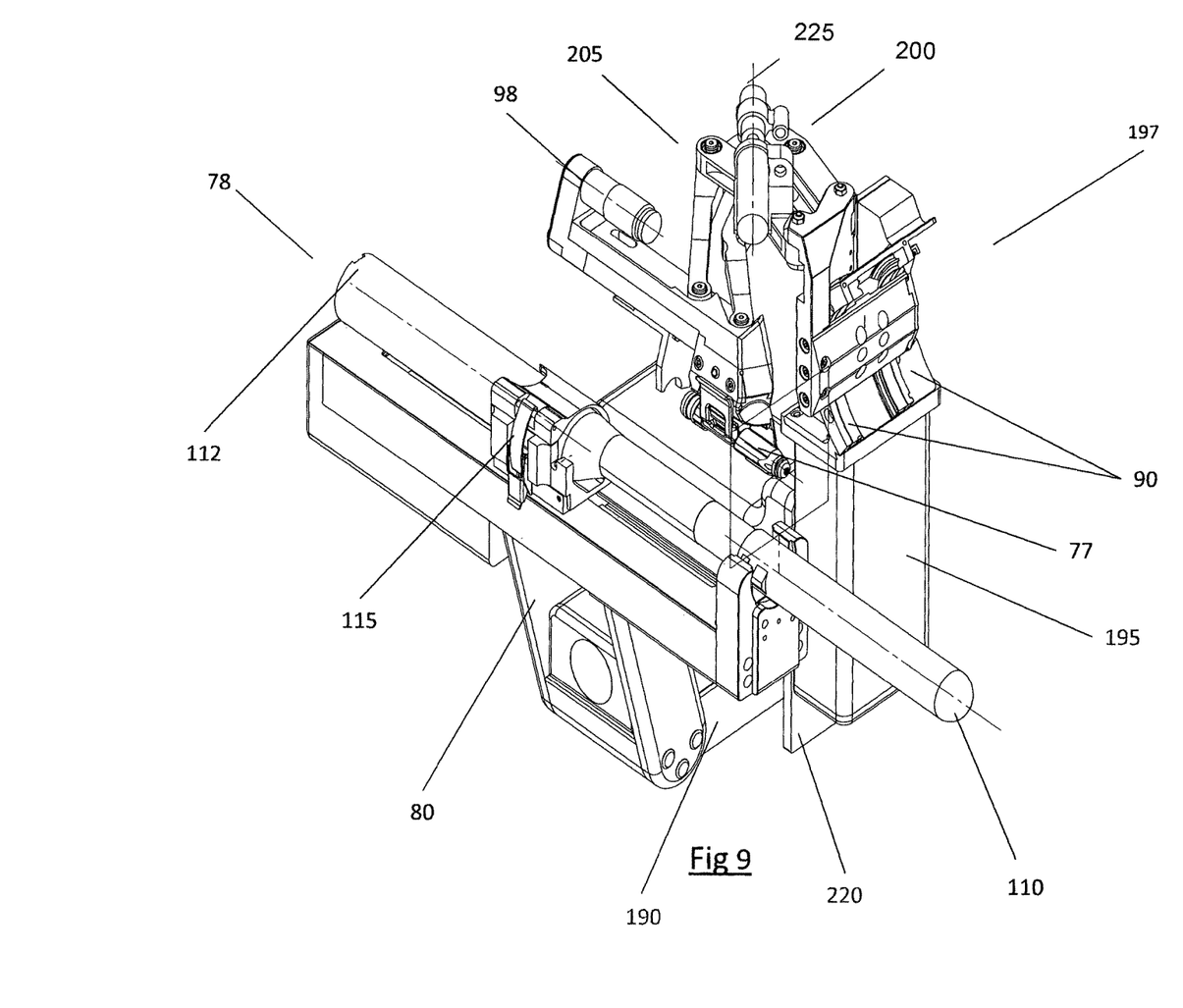
FIG. 9 is the front view of a biopsy and therapy device according to a further embodiment of the present invention.

FIGS. 9 to 11B show the apparatus (197) according to another embodiment of the present invention. In FIG. 9, the apparatus (197) is mounted on a supporting platform (80) which may be moved so as to place the probe (110) and rotary head (200) approximate to the patient. As with previous embodiments, the X-axis rotation (135) of the needling unit (77) is achieved by a pair of upper and lower radial sliding bearings or actuate slide (90), where this pair of radial sliding bearing is driven by a micro drive (98). In the new embodiment, the Y-axis rotation (140) of the needling unit (77) is achieved by a plurality of arms forming a rotational linkage (205) driven by a micro drive (225). These four sub units (77, 90, 205, and 225) will form the rotary head (200). The plurality of arms comprise a first pair of arms between the needling unit (77) and the drive (225) and a second pair of arms between the drive (225) and the arcuate slide (90). The two pairs of arms are mounted so as to each form a parallelogram linkage with the drive (225) therebetween to extend and retract the parallelogram linkages.

Figure 10A:
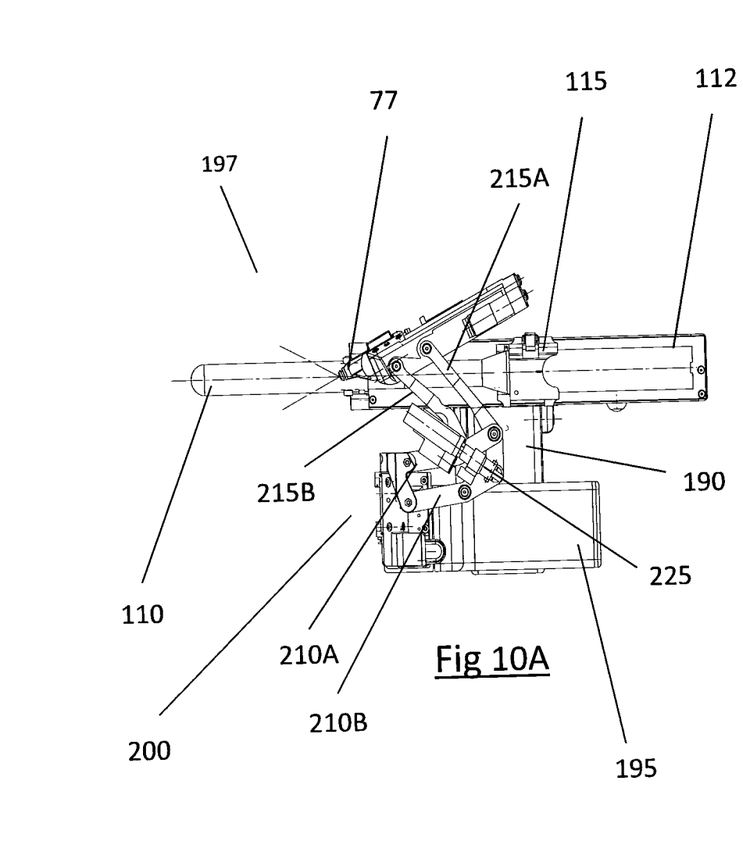
FIGS. 10A and 10B are plan views of the biopsy and therapy device of FIG. 9.
Figure 10B:
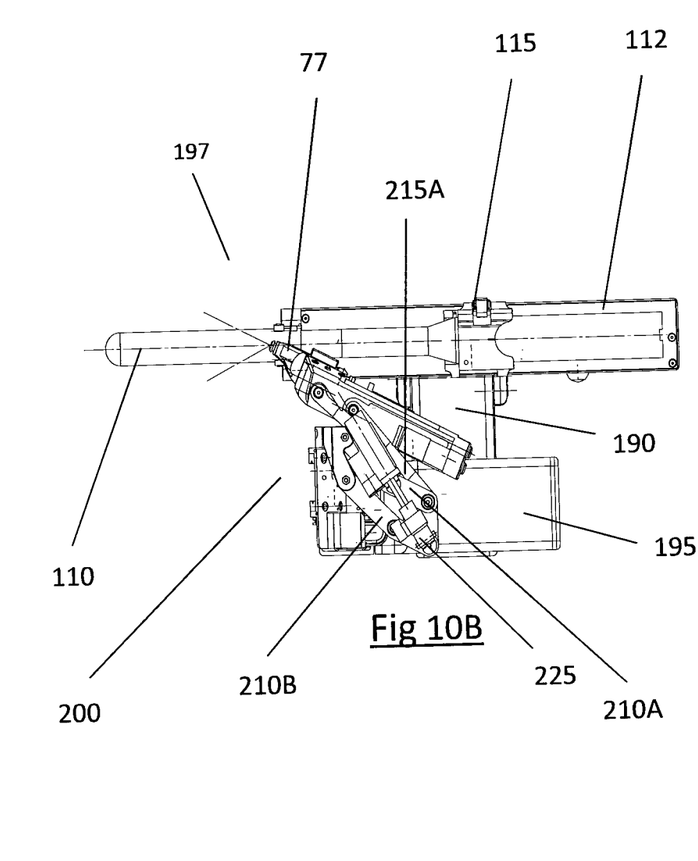
Figure 11A:
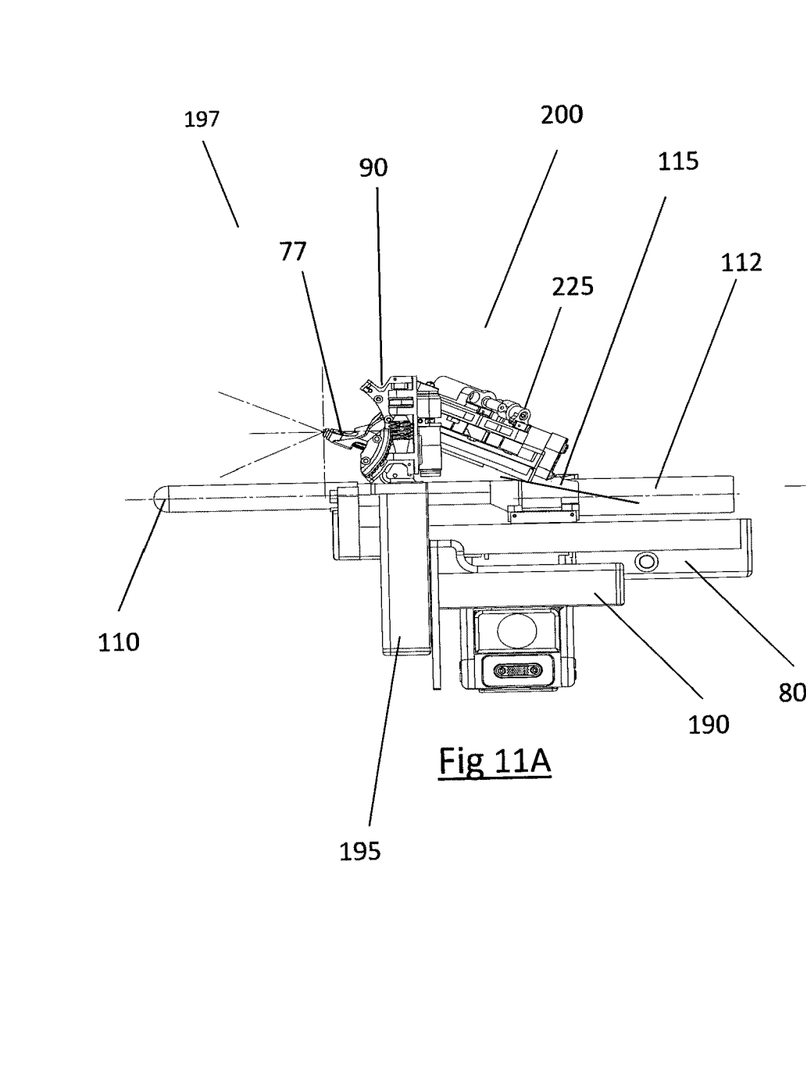
FIGS. 11A and 11B are elevation views of the biopsy and therapy device of FIG. 9.
Figure 11B:
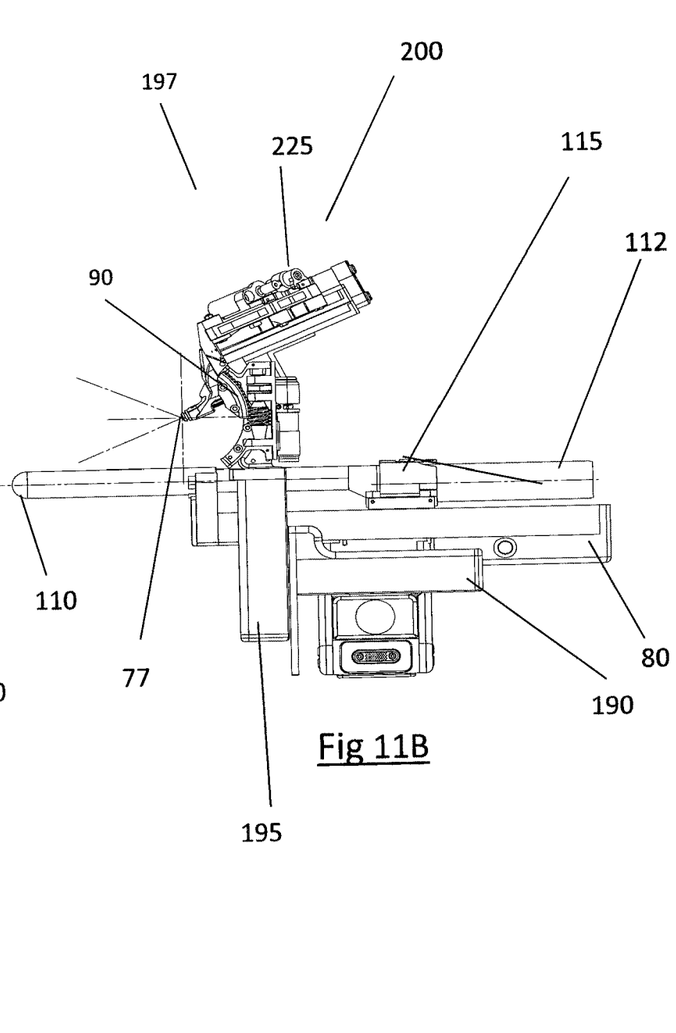
Figure 12:
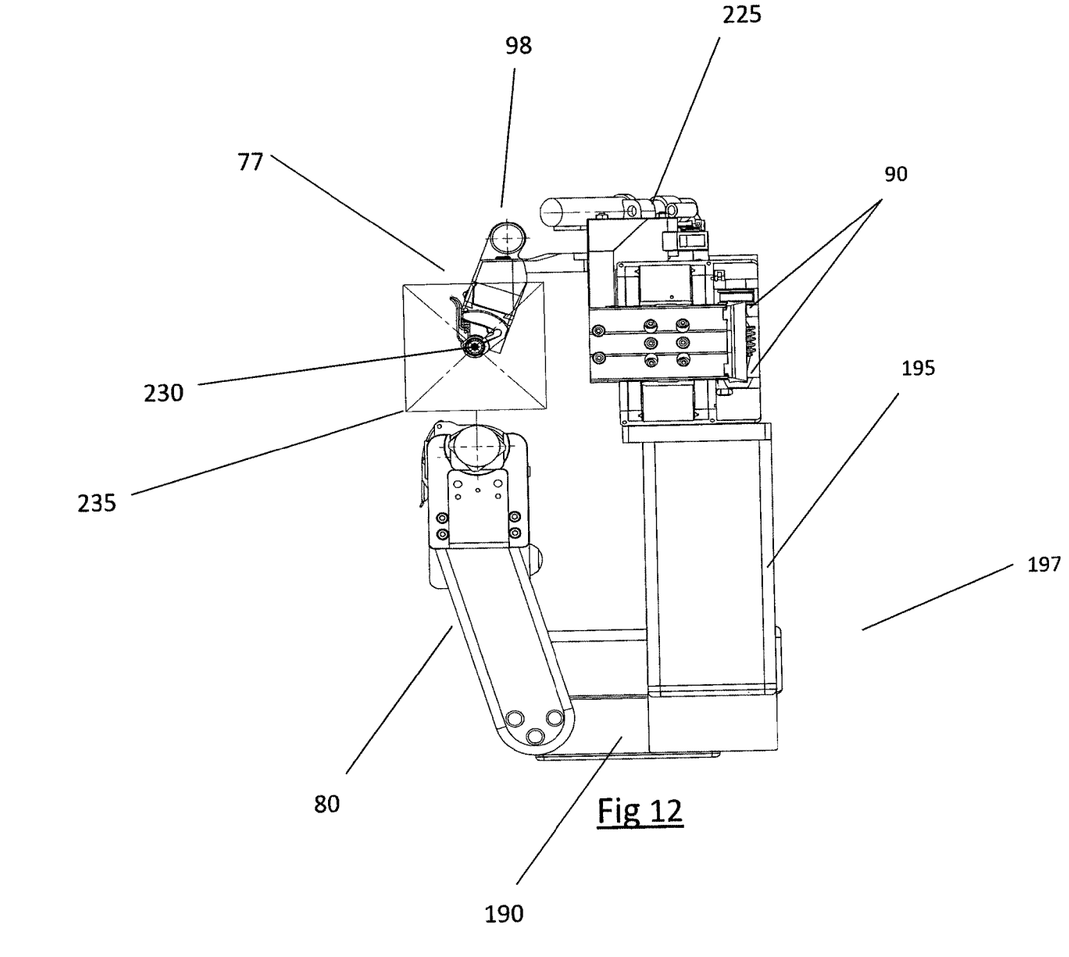
FIG. 12 is a front view of the biopsy and therapy device of FIG. 9.

FIGS. 10A and 10B are plan views of the apparatus (197). FIG. 10A illustrates the needling unit (77) projected to one extreme end of the Y-axis rotation (140). FIG. 10B illustrates the needling unit (77) retracted to the other extreme of the Y-axis rotation (140). These movements correspond to the movements described with reference to FIG. 4. The rotational linkage (205) is a mechanical linkage made of elongate metal members or arms (210A, 210B, 215A and 215B). Arm 215A extends from arm 210A and is in rotational engagement with one another. Similarly, arm 215B extends from arm 210B and is in rotational engagement with one another. Arms (210A, 210B, 215A and 215B) are arranged such that arms 215A and 215B can either extend at an angle from arms 210A and 210B on projection, as in FIG. 10A or, retract close to arms 210A and 210B such that the needling unit (77) moves to the other extreme of the Y axis rotation 140, as in FIG. 10B. Arms 210A and 210B are mounted to the arcuate slide (90) and a Y-axis linear slide (195) to which the acruate slide (90) is mounted. The needling unit (77), as part of the rotary head, is mounted to arms 215A and 215B. The arcuate slides are mounted perpendicular to the arms (210A, 210B, 215A and 215B) so that projection and retraction of the arms 210A and 210B in relation to arms 215A and 215B translates to rotation of the needing unit (77) about the respective X and Y axes creating an envelope 235 within the X-Y, or vertical, plane as seen in FIG. 12. The design and concept of this rotary head enables the whole needling unit (77) to rotate about a common virtual pivot point (230) illustrated in FIG. 12, thereby enhancing the reliability of the equipment during biopsy.

The invention claimed is:

1. A biopsy and therapy device comprising:
a needling unit for holding and inserting a biopsy needle;
an imaging module comprising an ultrasound probe and an actuator for moving the probe in a reciprocal action;
a first arcuate slide;
a second arcuate slide in sliding engagement with the first actuate slide and a linkage to which the first arcuate slide is mounted;
said linkage arranged to move the first and second arcuate slides within a vertical plane;
said needling unit mounted to said first and second arcuate slides, wherein the first and second arcuate slides are mounted perpendicular to each other so as to rotate the needling unit about respective first and second principal axes; and wherein the imaging module includes a probe sheath positioned on said probe and arranged to allow relative reciprocal motion with said probe.

2. The biopsy and therapy device according to claim 1, wherein the first and second arcuate slides are concentric about a pivot point.

3. The biopsy and therapy device according to claim 2, wherein said pivot point is located at a contact point of the needling unit.

4. The biopsy and therapy device according to claim 1, wherein each arcuate slide comprises a pair of radial sliding bearings.

5. The biopsy and therapy device according to claim 1, wherein the first and second arcuate slides form part of a rotary head.

6. The biopsy and therapy device according to claim 1, wherein the needling unit includes a needle holder for holding said biopsy needle during insertion, said needle holder including a recess for receiving said biopsy needle in a direction transverse to a direction of insertion.

7. The biopsy and therapy device according to claim 1, wherein said needling unit includes a needle stopper arranged to set a pre-determined depth of penetration of said biopsy needle.

8. The biopsy and therapy device according to claim 1, further including a drape for covering said biopsy and therapy device, said needling unit including a recess with which the drape is arranged to engage.

9. The biopsy and therapy device according to claim 1, wherein said biopsy and therapy device is arranged to conduct a biopsy procedure based upon one or more of the parameters: a needle insertion point defined as a coordinate position within said vertical plane, a first angle relative to the first principal axis, a second angle relative to the second principal axis and a depth of penetration of the biopsy needle.

* * * * *

UNITED STATES PATENT AND TRADEMARK OFFICE
CERTIFICATE OF CORRECTION

PATENT NO. : 11,490,880 B2
APPLICATION NO. : 16/685688
DATED : November 8, 2022
INVENTOR(S) : Yap et al.

It is certified that error appears in the above-identified patent and that said Letters Patent is hereby corrected as shown below:

In the Claims

Column 8, Line 3:
Delete "actuate", and insert --arcuate--.

Signed and Sealed this
Fourteenth Day of February, 2023

Katherine Kelly Vidal
*Director of the United States Patent and Trademark Office*